United States Patent [19]

Hui et al.

[11] Patent Number: 4,720,560
[45] Date of Patent: Jan. 19, 1988

[54] HYBRID ORGANOMETALLIC COMPOUNDS, PARTICULARLY FOR METAL ORGANIC CHEMICAL VAPOR DEPOSITION

[75] Inventors: Benjamin C. Hui, Peabody, Mass.; Jorg Lorberth, Weimar-Niederweimar, Fed. Rep. of Germany; Andreas A. Melas, Burlington, Mass.

[73] Assignee: Morton Thiokol, Inc., Chicago, Ill.

[21] Appl. No.: 664,645

[22] Filed: Oct. 25, 1984

[51] Int. Cl.$^4$ .............................................. C07F 5/00
[52] U.S. Cl. ....................................... 556/1; 556/129; 556/170; 556/187; 556/70
[58] Field of Search ................ 556/1; 260/429.9, 431, 260/429 R, 448 A, 665 R; 568/7, 1

[56] References Cited

U.S. PATENT DOCUMENTS

| | | | |
|---|---|---|---|
| 2,266,776 | 12/1941 | Leum | 568/1 X |
| 2,818,416 | 12/1957 | Brown et al. | 260/429 CY |
| 2,969,382 | 1/1961 | Mangham | 568/1 X |
| 3,026,356 | 3/1962 | Brown | 568/7 |
| 3,097,066 | 7/1963 | Köster et al. | 568/1 X |
| 3,161,686 | 12/1964 | Brown | 568/1 |
| 3,247,261 | 4/1966 | D'Alelio | 260/665 R |
| 3,755,478 | 8/1973 | Kamienski | 260/665 R |
| 3,755,479 | 8/1973 | Marlett et al. | 260/665 R |
| 4,447,369 | 5/1984 | Ashby | 260/665 R |

FOREIGN PATENT DOCUMENTS 121478 11/1974 Japan .

OTHER PUBLICATIONS

JACS 97(7) 1674 (1975).
Smith, J. Organometallic Chem., 76, pp. 171 & 178 (1974).
Chemical Abstracts, 95, 168370f (1981).
Baker et al., J. Org. Chem., 46, 4127–4130 (1981).
Chemical Abstracts, 99, 212623z, Ash et al. (1983).
Organometallics, 2, 1859–1866 (1983).
Nesmeyanov et al., The Organic Compounds of Boron, Aluminum, Galluimo, Indium & Thalliumo, North Holland Pub. Co., Amsterdam, pp. 103, 152, 555, 157 and 158 (1967).
Dub, Organometallic Compounds, Springer Verlag, Berlin, vol. III, p. 542 (1962).
Sheverdina et al., The Organic Compounds of Zinc and Cadmium, North–Holland Publ. Co., Amsterdam, vol. 3, pp. 22 to 25, 173 & 174 (1967).

(List continued on next page.)

Primary Examiner—Helen M. S. Sneed
Attorney, Agent, or Firm—George Wheeler; Gerald K. White

[57] ABSTRACT

Compounds having the molecular formula:

$$MR_x$$

wherein x is an integer from 2 to 4 inclusive, each said R substituent is independently selected from hydride, lower alkyl, phenyl, alkyl-substituted phenyl, cyclopentadienyl, and alkyl substituted cyclopentadienyl, at least two of said R substituents are different, and M is an element selected from Groups 2B or 3A of the Periodic Table, Bismuth, Selenium, Tellurium, Beryllium, and Magnesium, but excluding Aluminum, Bismuth, Selenium, and Tellurium if any R is hydride. The hybrid compound is used for metal organic chemical vapor deposition. The invention also includes a metal organic chemical vapor deposition process employing a hybrid of first and second compounds having the above formula, but wherein the R substituents of each compound can be like or unlike and M is selected from Groups 2B, 2A, 3A, 5A, and 6A of the Periodic Table except for Carbon, Nitrogen, Oxygen, and Sulfur. The hybrid composite compound has different properties than the first and second compounds, and thus can be more suitable for a particular metal organic chemical vapor deposition process.

19 Claims, 6 Drawing Figures

OTHER PUBLICATIONS

Nesmeyanov et al., Methods of Elements Organic Chemistry, North-Holland Publ. Co., Amsterdam, vol. 4, pp. 289–301 (1967).

Hagihara et al., Handbook of Organometallic Compounds, W. A. Benjamin, Inc., N.Y., pp. 47, 49, 55, 106, 114, 120, 121, 125, 127, 134, 171, 172, 176, 189, 192, 205, 756, 757, 762, 795–798 & 812 (1968).

Mole et al., Organoaluminum Compounds, Elsevier Publ. Co., N.Y., pp. 103, 104, 152, 157, 158, 162, 287, 288, 399, 414, 419 (1972).

Kaufman, Handbook of Organometallic Compounds, D. Van Nostrand Co., Inc., N.Y., pp. 35 to 37, 206 & 1397, 1491, 1492 and 1497 (1961).

Wilkinson, et al., Comprehensive Organometallic Chemistry, vol. 1 (1982), pp. 687, 688, 708.

HYBRID ORGANOMETALLIC COMPOUNDS, PARTICULARLY FOR METAL ORGANIC CHEMICAL VAPOR DEPOSITION

TECHNICAL FIELD

This invention relates to organometallic compounds comprising elements from Group 3A of the Periodic Table and mixed organic substituents selected from lower alkyl, hydride, phenyl, alkyl-substituted phenyl, cyclopentadienyl, and alkyl-substituted cyclopentadienyl. This invention also relates to metal organic chemical vapor deposition (MOCVD) processes employed in the optoelectronics industry.

BACKGROUND ART

MOCVD is a method for depositing thin metal or metal compound films on a silicon or other substrate. (In the present disclosure "metal" includes all of the elements of Groups 2B, 2A, 3A, 4A, 5A, and 6A of the Periodic Table except Carbon, Nitrogen, Oxygen, and Sulfur.) The deposited films can be sources of doping impurities which are driven into the substrate, or the films themselves can have different electrical or optical properties than the substrate. These films are used to make laser diodes, solar cells, photocathodes, field effect transistors and other discrete devices, in fiber optic communications, microwave communications, digital audio disc systems, and other advanced optoelectronic technologies. The properties of the film depend on the deposition conditions and the chemical identity of the deposited film.

A special advantage of MOCVD is that organometallic compounds can be found which have much higher vapor pressures at moderate temperatures than the corresponding metals, and which decompose to release the corresponding metals or form compounds thereof at the 550 to 700 degrees Celsius deposition temperatures which should not be exceeded during fabrication.

Typical apparatus currently in use for MOCVD comprises a bubbler which contains a supply of the organometallic compound chosen for a particular process, a reactor or deposition chamber which contains the substrate on which a film is to be deposited, a source of a carrier gas which is inert to the organometallic compound in the bubbler and either inert or reactive to the compound in the deposition chamber, and optionally sources of other reactants or dopants supplied to the reaction chamber. The bubbler and contents are maintained at a constant and relatively low temperature which typically is above the melting point of the organometallic compound but far below its decomposition temperature. The deposition chamber is typically maintained at a much higher temperature, such as about 550 to 700 degrees Celsius, at which the organometallic compound readily decomposes to release its constituent metal. To operate the MOCVD apparatus, the carrier gas is introduced into the bubbler under the surface of the organometallic compound. Rising bubbles of the carrier gas provide a large, constant contact surface and thus uniformly vaporize the organometallic compound.

The carrier gas and vapor collected in the headspace of the bubbler are continuously directed to the deposition chamber.

While it is possible to vaporize a sublimable solid organometallic compound in a bubbler, it is difficult to control its rate of vaporization. The surface area of a solid exposed to the carrier gas changes as vaporization proceeds. In contrast, a liquid contained in a bubbler with substantially vertical walls presents the same surface area of a solid to the carrier gas so long as the flow and bubble size of the carrier gas remains steady. Thus, organometallic compounds for MOCVD desirably are liquids at or slightly above room temperature (from about −20° C. to about 40° C.). Such compounds also should have a vapor pressure of at least about 1.0 torrs at the bubbler temperature, boil and decompose at temperatures substantially exceeding the bubbler temperature, and decompose readily at the temperature encountered in the deposition chamber.

GALLIUM

Triethylgallium
Trimethylgallium

INDIUM

Trimethylindium
Triethylindium

Because there are few organometallic compounds of Gallium and Indium, there often will be no compound of these metals which is well suited to MOCVD. Furthermore, the previously listed compounds do not include more than one type of organic substituent on a given molecule. For these elements in particular, it is difficult to select a useful candidate having the necessary properties for MOCVD.

Another factor complicates the selection of a workable organometallic compound for MOCVD: structurally related organometallic compounds often do not form homologous series. Many organometallic compounds characteristically exist in only one form, for example, as monomers, dimers, trimers, tetramers, or higher polymers. Structurally similar compounds often have different characteristic forms, and thus much different or inconsistent vapor pressures, melting points, and decomposition temperatures.

As a particular case in point, consider the two known compounds of indium—trimethylindium and triethylindium. Both of these compounds have been used to deposit Indium containing films. (See: 1. Manasevit and Simpson, *J. Electrochem. Soc.*, 118, C291 (1971); 120, 135 (1973). 2. Bass, *J. Crystal Growth*, 31, 172 (1975). 3. Duchemin, et al., Paper 13, 7th *Intern. Symp, on GaAs and Related Compounds*, Clayton, MD, September, 1978.) Though they are structurally similar, the respective melting points, vapor pressures at 30 degrees Celsius and decomposition temperatures of these compounds are inconsistent with what would be expected of homologs, as illustrated by Table I below:

TABLE I

| PROPERTY | TRIETHYLINDIUM | TRIMETHYLINDIUM |
| --- | --- | --- |
| Melting Point | −32° C. | 88° C. |
| Vapor Pressure at 30° C. | 0.8 torrs | 7.2 torrs |
| Decomposition temperatures | 40° C. | 260° C. |

Trimethylindium is believed to characteristically form a tetramer and triethylindium is believed to characteristically form a monomer at room temperature.

This difference is believed to underlie their inconsistent properties.

The preceding table illustrates that trimethylindium is a solid at temperatures employed in bubblers, and has a vapor pressure of sublimation which is undesirably low. Trimethylindium has been vaporized by providing two bubblers in series to better control the amount of entrained vapor. The apparatus necessary for this two bubbler procedure is more expensive and complex, and yet provides less control of the partial pressure of trimethylindium, than apparatus used to vaporize a liquid from a single bubbler. Triethylindium has an even lower vapor pressure at 30 degrees Celsius than trimethylindium, and is also less thermally and chemically stable than trimethylindium. Triethylindium starts to decompose to Indium at 35 degrees Celsius, and at an even lower temperature in the presence of hydrogen—the typical carrier gas. The vaporization of triethylindium thus must take place at a temperature approaching its decomposition temperature, and even then the deposition rate is undesirably low. The lack of homology in these Indium compounds and the small number of known Indium compounds have prevented those of ordinary skill in the art from selecting an optimal compound for Indium MOCVD.

SUMMARY OF THE INVENTION

The invention is a genus of compounds useful for metal organic chemical vapor deposition, defined by the molecular formula:

$$MR_x$$

x is 3, each said R substituent is independently selected from lower alkyl, phenyl, alkyl-substituted phenyl, cyclopentadienyl, and alkyl-substituted cyclopentadienyl, and at least two of the R substituents are different. M is selected from Gallium and Indium.

DESCRIPTION OF PREFERRED EMBODIMENTS

Figure 1:
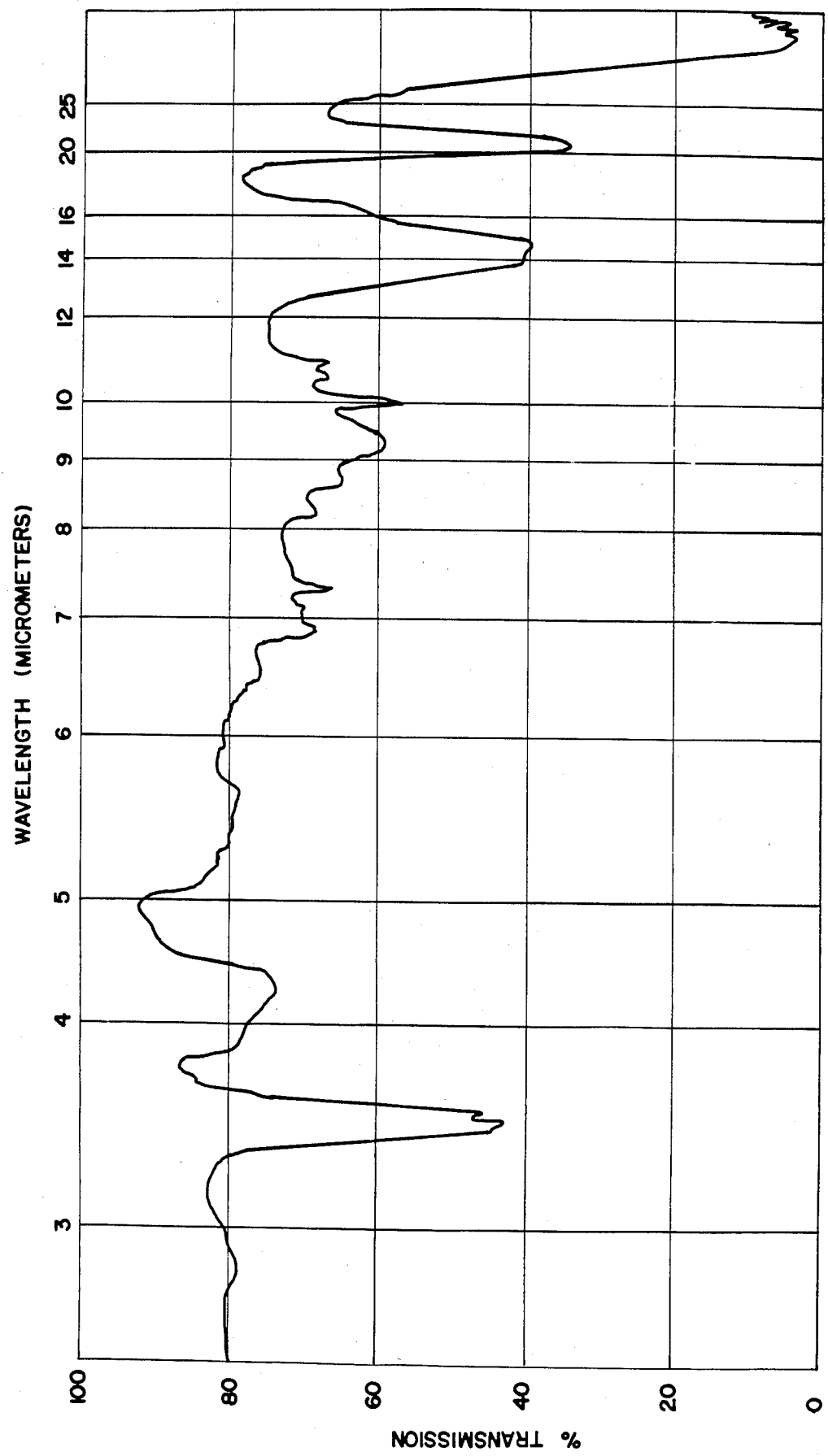
FIG. 1 is an infrared absorption spectrum of dimethylethylindium.

The novel compounds of the present invention are defined generically in the first paragraph of the "SUMMARY OF THE INVENTION" section of the specification. A representative element contemplated for use herein, and further illustrated in the examples, is Indium.

R substituents contemplated for use in the novel compounds include, lower alkyl, phenyl, alkyl-substituted phenyl, cyclopentadienyl, and alkyl substituted cyclopentadienyl. Lower alkyl is defined herein as a substituent having from one to four carbon atoms, and specifically includes methyl, ethyl, n-propyl, isopropyl, n-butyl, isobutyl, and t-butyl. Alkyl substituted phenyl as defined herein includes alkyl substituted phenyl and phenyl substituted alkyl, alkyl being lower alkyl as exemplified above. Specific substituents contemplated within the meaning of alkyl substituted phenyl are as follows: benzyl; tolyl in ortho, meta, or para positions with respect to the metal; xylyl, including orientations in which the methyl substituents are ortho with respect to each other and respectively ortho and meta or meta and para with respect to the metal, or if the methyl substituents are meta, situations in which the methyl substituents are respectively ortho and ortho, or ortho and para, or meta and meta with respect to the metal atom, and if the methyl substituents are para, the situation in which the methyl substituents are ortho and meta to the metal substituent of the phenyl; ethylphenyl, isopropylphenyl, butylphenyl, isobutylphenyl, t-butylphenyl, these substituents being in ortho, meta, or para relation to the metal atom; and any other phenyl having one or more of the alkyl substituents previously defined. Alkyl substituted cyclopentadienyl as defined herein includes alkyl substituted cyclopentadienyl and cyclopentadienyl substituted alkyl, alkyl being lower alkyl as exemplified above. Specific substituents contemplated within the meaning of alkyl-substituted cyclopentadienyl are as follows: methylcyclopentadienyl, 4-(cyclopentadienyl)-n-butyl, pentamethylcyclopentadienyl, and cyclopentadienyl substituted by up to six like or different lower alkyl groups and linked directly or by one of the lower alkyl groups to the selected metal atom.

The generic invention includes any metal as previously defined combined with any two or more R substituents as previously defined. The genus is limited, however, by the requirement that at least two different R substituents must be associated with each metal atom.

Exemplary species contemplated herein include the following:

Hybrid organometallic compounds can be produced by mixing organometallic compounds containing the respective substituents of the hybrid; by reacting a halogen substituted organometallic compound with an alkylating or arylating agent to add an unlike substituent; by reacting the metal for which an organometallic hybrid compound is desired with mixtures of organic halides; by substituting a more active metal for a less active metal in an organometallic hybrid compound of the less active metal; or by other means.

To practice the mixing method described in the preceding paragraph, first and second organometallic compounds are first selected. Each reactant has the formula:

$$MR_x$$

in which R and x are defined as previously, except that each R of the first compound can be identical, and each R of the second compound can be identical, but at least one R substituent of the first compound is different than at least one R substituent of the second compound. The first and second compounds are then mixed together and allowed to equilibrate at a temperature below the lower of the boiling points of the reactants and products, preferably from 0°–30° Celsius. A nonreactive solvent such as benzene, hexane, ether, tetrahydrofuran, etc. is optional. The result of this exchange reaction will typically be a major proportion of a hybrid organometallic compound according to the invention, in which the several R substituents are present in roughly the same proportions as in the reaction mixture containing the first and second reactants. Minor proportions of the reactants and of other organometallic products may also be present. The desired product can be isolated by distillation, crystallization, or other well known processes. Alternatively, the product mixture can be used for MOCVD without isolating a pure hybrid product. The following equations illustrate reactions of this type in which stoichiometric proportions of the reactants provide a major proportion of the indicated product:

$$2(CH_3)_3In(s) + (C_2H_5)_3In(l) \rightarrow 3(CH_3)_2C_2H_5In(l)$$

$$2(C_2H_5)_3In(l) + (CH_3)_3In(s) \rightarrow 3(C_2H_5)_2CH_3In(l)$$

In the second synthetic method identified above, a halogenated organometallic compound having one of the desired alkyl, phenyl, alkyl substituted phenyl, cyclopentadienyl, or alkyl substituted cyclopentadienyl substituents is reacted with an alkylating or arylating agent. The alkyl or aryl group of the alkylating or arylating agent then replaces the halogen substituent of the organometallic compound. Typical alkylating agents for use herein include such materials as methyllithium, ethylmagnesium bromide, or lithium aluminum hydride. Examples of these synthetic reactions and analogous reactions of different metals are set forth in the three following equations:

$$(C_2H_5)_2InCl + CH_3Li \rightarrow CH_3(C_2H_5)_2In + LiCl$$

$$CH_3ZnBr + C_2H_5MgBr \rightarrow CH_3C_2H_5Zn + MgBr_2$$

$$(CH_3)_2GaCl + LiAlH_4 \rightarrow (CH_3)_2GaH + LiAlH_3Cl$$

The reaction of metals with mixtures of organic halides to produce hybrid organometallic compounds is illustrated by the following reaction:

$$CH_3Br + C_2H_5Br + 2Se \rightarrow CH_3C_2H_5Se + SeBr_2$$

The metal displacement reaction suggested previously is exemplified by the following reaction:

$$(C_6H_5)_3(C_2H_5)Pb + 2Zn \rightarrow (C_6H_5)_2Zn + (C_6H_5)C_2H_5Zn + Pb$$

In the above reaction, it will be appreciated that the metal of the organometallic reactant must be a less active metal than the substituting metal.

Other methods ordinarily used in organometallic synthesis, such as those discussed on pages 345-348 and 365-366 of Roberts and Caserio, *Basic Principles of Organic Chemistry*, W. A. Benjamin Inc. (New York: 1964) can also be adapted to synthesize the hybrid organometallic compounds defined herein.

As indicated previously, the present compounds have utility as reactants in MOCVD. Preferred reactants for this utility have a melting point of less than about 30 degrees Celsius, have a vapor pressure of at least 1.0 torrs at a temperature within the bubbler temperature range of from about minus 20 degrees Celsius to about 40 degrees Celsius, are stable at the indicated bubbler temperatures but readily decompose at a deposition chamber temperature of from about 550 to about 700 degrees Celsius, and are inert at bubbler temperatures with respect to at least one carrier gas such as hydrogen, nitrogen, or helium.

The present compounds also have utility for the preparation of other such compounds within the scope of the present invention. For example, a hybrid organometallic compound which does not have a desirable decomposition temperature may be reacted with another organometallic compound to produce a new hybrid.

The present compounds also have utility in organic synthesis and as catalysts, for example in Ziegler-Natta processes.

The ultimate utility of these compounds, employed in MOCVD, is to provide a coating of the constituent metal, or (in combination with other reactants introduced in the deposition chamber) to provide coatings of metal oxides, nitrides, III-V compounds, and so forth. The Group 3A and 5A metal hybrid organometallic compounds can also be used as dopants.

EXAMPLES

The following examples are provided to further exemplify and demonstrate the use of the present invention. The examples do not limit the scope of the invention, which is defined by the claims found at the end of the specification.

EXAMPLE 1

Figure 2:
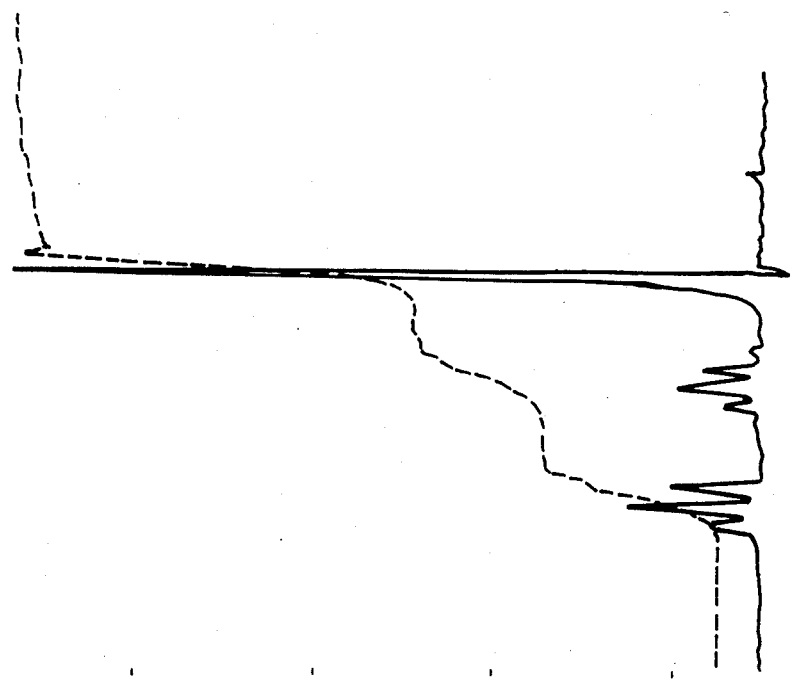
FIG. 2 is a proton nuclear magnetic resonance spectrum of dimethylethylindium.

SYNTHESIS OF DIMETHYLETHYLINDIUM 3.00 ml. of triethylindium (3.78 g., 0.0187 mol) was added to 5.988 g. (0.0374 mol) of trimethylindium in a 50 ml. flask in a glove bag under an Argon atmosphere. The reagents were stirred at room temperature overnight. Reaction was essentially complete when all of the trimethylindium was fully reacted, leaving no residual solids. The resulting clear liquid was then distilled under full vacuum, (about 1.5 torrs pressure). Some of the resulting dimethylethylindium distilled over at room temperature, or about 23 degrees Celsius. Gentle heating caused the rest to come over at 25 degrees Celsius, this temperature being measured at the distillation head. The resulting product had a melting point of about 5 to 7 degrees Celsius and a boiling point of 23°–25° C. at 1.5 torrs, which is unexpectedly different than the respective melting points and boiling points of trimethylindium and triethylindium. Proton nuclear magnetic resonance and infrared spectra were taken, and are presented as FIGS. 1 and 2 forming a part of this specification. For comparison, the NMR spectra of trimethylindium and triethylindium are presented as FIGS. 5 and 6. The infrared spectrum is not believed to distinguish the product compound, but the NMR spectrum of dimethylethylindium is characterized by peaks at delta +1.27 (triplet representing ethyl); +0.37 (quartet representing ethyl); and −0.36 (singlet representing methyl). Integration of the areas under the peaks provides the ratio of methyl to ethyl groups, which is 2:1.

EXAMPLE 2

Figure 4:
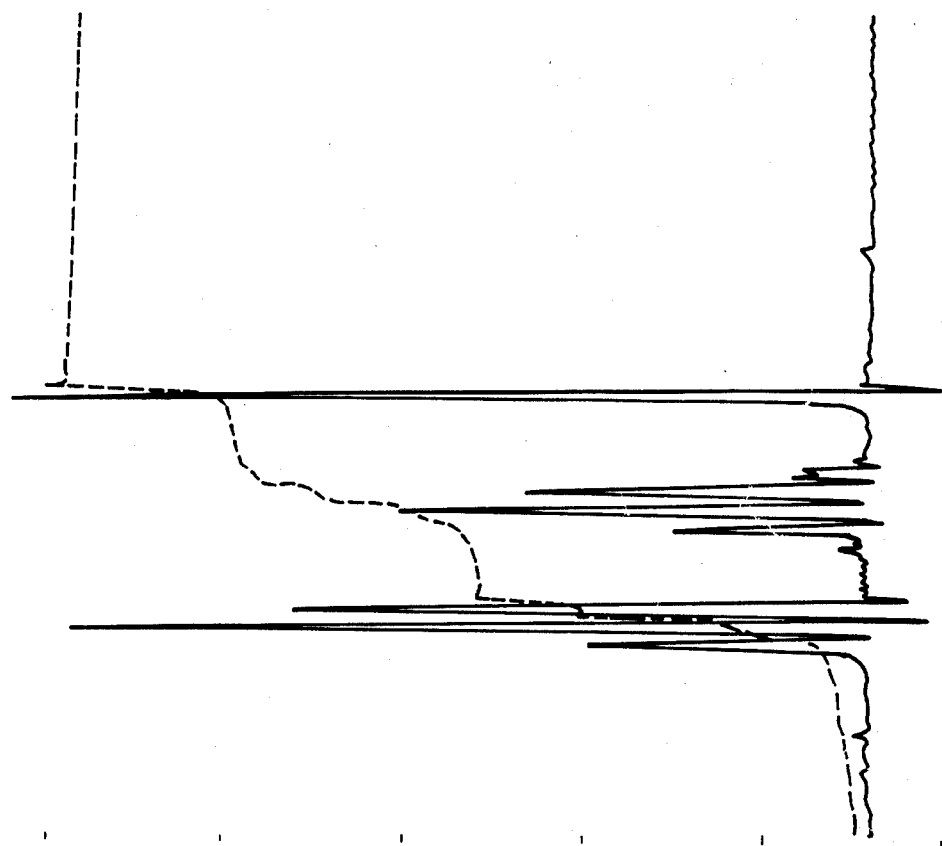
FIG. 4 is a proton nuclear magnetic resonance spectrum of diethylmethylindium.
Figure 3:
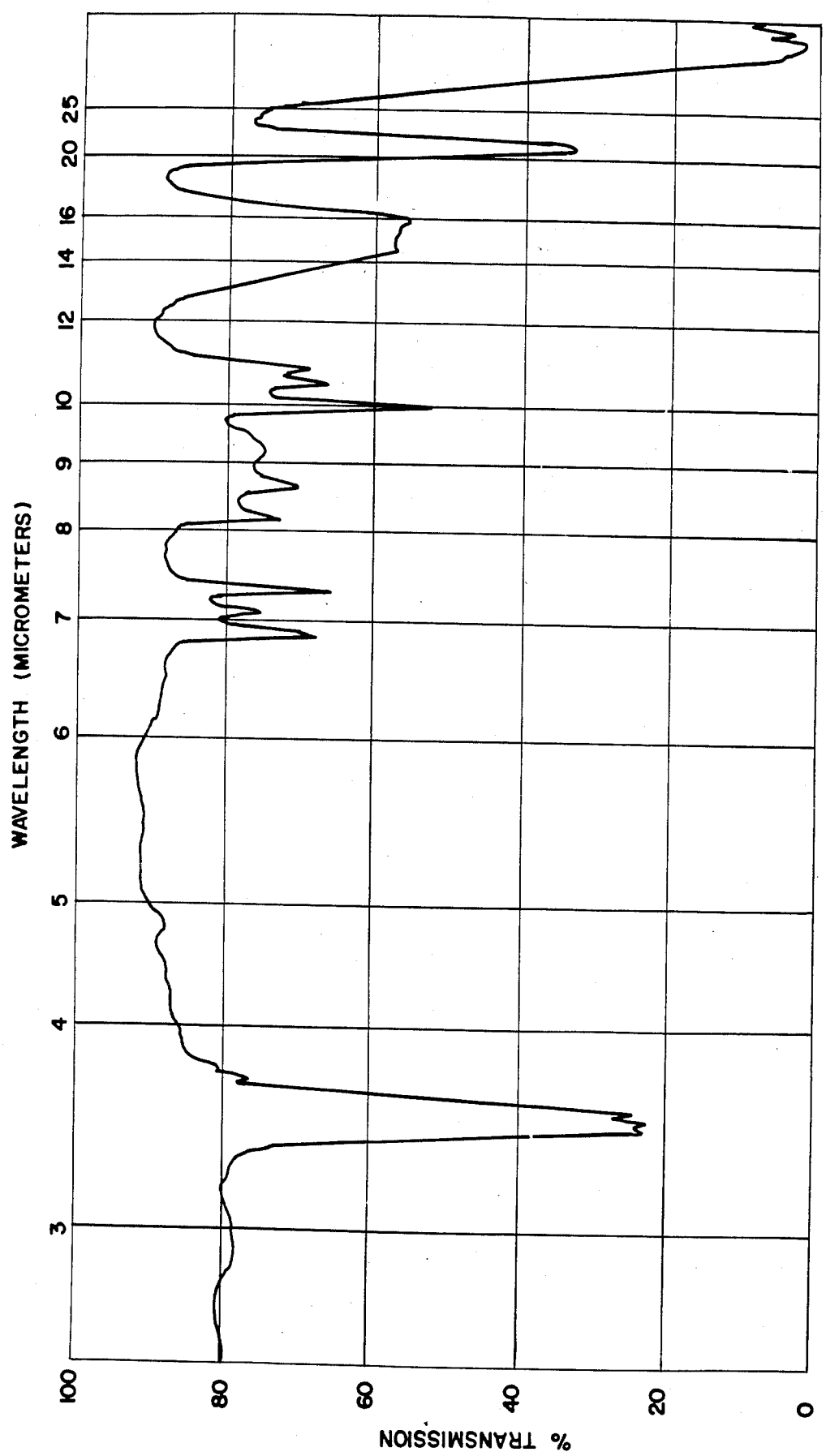
FIG. 3 is an infrared absorption spectrum of diethylmethylindium.

SYNTHESIS OF DIETHYLMETHYLINDIUM 5.00 ml. (6.30 g., 0.0312 mol.) of triethylindium was added to 2.495 g. (0.0156 mol.) of trimethylindium in a 50 ml. flask in a glove bag containing an Argon atmosphere. The mixture was stirred overnight and then distilled at 33 to 35 degrees Celsius under full vacuum as previously defined. The distillate was a clear, colorless liquid. NMR and IR spectra were taken, and are provided as FIGS. 3 and 4 herein. The NMR is characterized by peaks at delta values of +1.28 (triplet ethyl); +0.39 (quartet ethyl); and −0.39 (singlet methyl). An integration of the areas under the peaks shows a ratio of ethyl to methyl of 1.94:1. The melting point was found to be below about 3 degrees Celsius, as the product failed to solidify when the container was placed in ice water.

EXAMPLE 3

PROPERTIES OF TRIMETHYLINDIUM AND TRIETHYLINDIUM (PRIOR ART)

Figure 5:
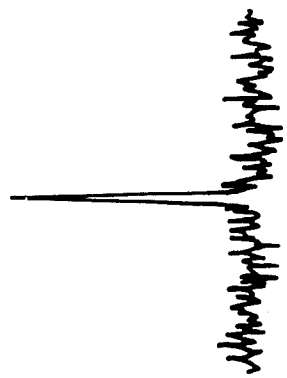
FIG. 5 is a proton nuclear magnetic resonance spectrum of trimethylindium, a prior art compound.

FIG. 5 is the NMR spectrum of trimethylindium, characterized by a singlet methyl peak at a delta value of −0.20. The melting point of trimethylindium is 88 degrees Celsius.

Figure 6:
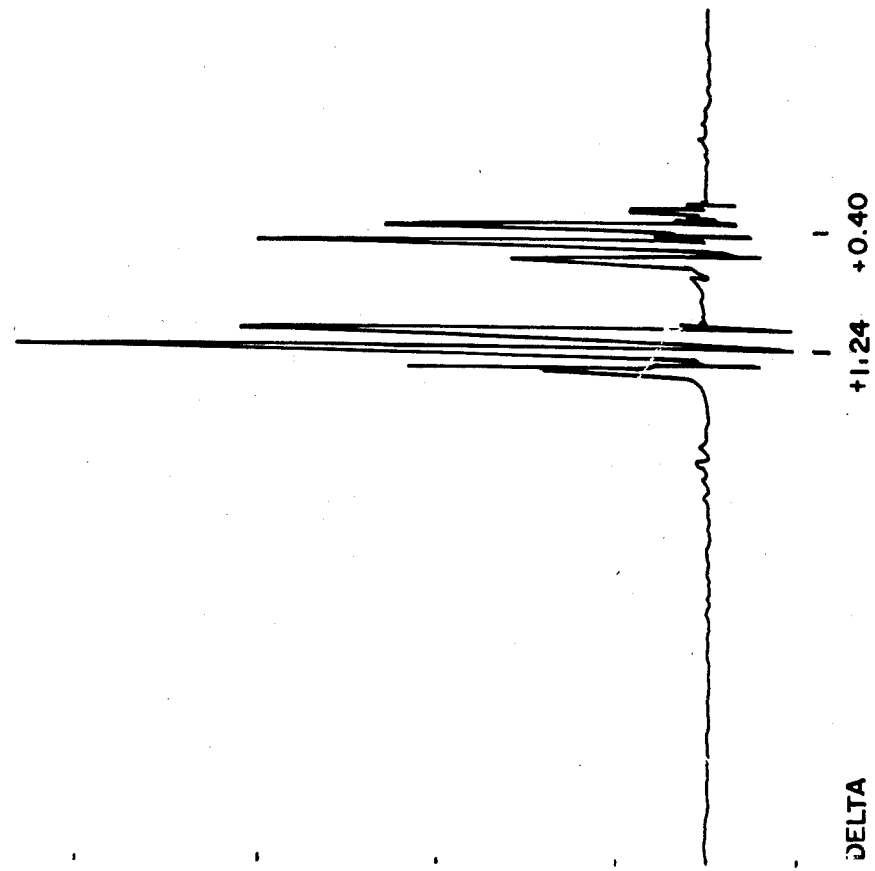
FIG. 6 is a proton nuclear magnetic resonance spectrum of triethylindium, a prior art compound.

FIG. 6 is the NMR spectrum of triethylindium, characterized by peaks at delta values of +1.24 (triplet ethyl) and +0.40 (quartet ethyl). The melting point of triethylindium is −32 degrees Celsius.

EXAMPLE 4

SYNTHESIS OF OTHER HYBRID ORGANOMETALLIC COMPOUNDS

The procedure of Examples 1 and 2 is followed for the species previously listed herein and species of analogous metals. The reactants mixed to form the indicated species are provided in Table II below:

TABLE II

| PRODUCT | REACTANT 1 | REACTANT 2 |
|---|---|---|
| $C_2H_5ZnCH_3$ | $(CH_3)_2Zn$ | $(C_2H_5)_2Zn$ |
| $CH_3CdC_2H_5$ | $(CH_3)_2Cd$ | $(C_2H_5)_2Cd$ |
| $CH_3HgC_6H_5$ | $(CH_3)_2Hg$ | $(C_6H_5)_2Hg$ |
| $(CH_3)_2BC_2H_5$ | $(CH_3)_3B$ | $(C_2H_5)_3B$ |
| $CH_3Al(C_6H_5)_2$ | $(CH_3)_3Al$ | $(C_6H_5)_3Al$ |
| $CH_3Al(C_6H_5CH_3)_2$ | $(CH_3)_3Al$ | $Al(C_6H_5CH_3)_3$ |
| $(CH_3)_2GaC_2H_5$ | $(CH_3)_3Ga$ | $(C_2H_5)_3Ga$ |
| $(CH_3)_2InC_2H_5$ | $(CH_3)_3In$ | $(C_2H_5)_3In$ |
| $(C_2H_5)_2InCH_3$ | $(CH_3)_3In$ | $(C_2H_5)_3In$ |
| $(CH_3)_2TlC_2H_5$ | $(CH_3)_3Tl$ | $(C_2H_5)_3Tl$ |
| $(C_4H_9)_2PC_6H_5$ | $(C_4H_9)_3P$ | $(C_6H_5)_3P$ |
| $(C_2H_5)_2As(CH_2C_6H_5)$ | $(C_2H_5)_3As$ | $As(CH_2C_6H_5)_3$ |
| $(CH_3)(C_4H_9)(C_6H_5)Sb$ | $(CH_3)_2(C_6H_5)Sb$ | $(C_4H_9)_3S_6$ |
| $CH_3Bi(CH_2CH_3CH_3)_2$ | $(CH_3)_3Bi$ | $(CH_3CH_2CH_2)_3Bi$ |
| $(CH_3)(C_2H_5)Se$ | $(CH_3)_2Se$ | $(C_2H_5)_2Se$ |
| $CH_3TeC_2H_5$ | $(CH_3)_2Te$ | $(C_2H_5)_2Te$ |
| $((CH_3)_2CHCH_2)CH_3AlH$ | $((CH_3)_2CHCH_2)_2AlH$ | $(CH_3)_3Al$ |
| $(C_2H_5)CH_3AsH$ | $(CH_3)_2AsH$ | $(C_2H_5)_3As$ |
| $(C_2H_5)SeH$ | $(C_2H_5)_2Se$ | $SeH_2$ |
| $(C_6H_5)MgCH_3$ | $C_6H_5)_2Mg$ | $(CH_3)_2Mg$ |
| 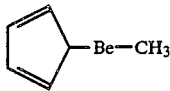 | 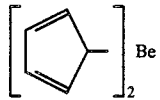 | $(CH_3)_2Be$ |

EXAMPLE 5

MOCVD PROCESS

Methyldiethylindium prepared as described previously is placed in a bubbler and suitably interconnected with a source of hydrogen gas and a deposition chamber. The chamber is also supplied with phosphine gas. The bubbler is maintained at 20 degrees Celsius using a suitable heat source, the deposition chamber is maintained at 650 degrees Celsius, and an Indium Phosphide substrate is supported within the deposition chamber. The entraining hydrogen is delivered at 100 cubic centimeters per minute (at standard temperature and pressure). The partial pressure of hydrogen in the deposition chamber is atmospheric pressure, and the partial pressure of methyldiethylindium is about 10 torrs, the partial pressure of phosphine being atmospheric pressure. After about 30 minutes of deposition, a coating of indium phosphide approximately 2 microns thick, uniform in composition and thickness, is found to be deposited on the substrate.

What is claimed is:

1. A compound having the molecular formula:

$$MR_x$$

wherein x is 3, each said R substituent is independently selected from lower alkyl, phenyl, alkyl-substituted phenyl, cyclopentadienyl, and alkyl-substituted cyclopentadienyl, at least two of said R substituents are different, and M is an element selected from Gallium and Indium, excluding dimethylcyclopentadienylgallium, dimethylcyclopentadienylindium, diethylcyclopentadienylgallium, and diethylcyclopentadienylindium.

2. The invention of claim 1, wherein M is Indium.
3. The invention of claim 2, wherein each R substituent is lower alkyl.
4. The invention of claim 3, wherein at least one said R substituent is methyl.
5. The invention of claim 4, wherein two said R substituents are methyl.
6. The invention of claim 5, wherein the remaining said R substituent is ethyl.
7. The invention of claim 3 wherein at least one said R substituent is ethyl.
8. The invention of claim 7, wherein two said R substituents are ethyl.
9. The invention of claim 8, wherein the remaining said R substituent is methyl.
10. A monomeric compound according to claim 1, consisting essentially of dimethylethylindium.
11. A monomeric compound according to claim 1, consisting essentially of diethylmethylindium.
12. A compound selected from:
methylbenzyltelluride;
dimethylethylthallium;
methylphenylgallium hydride; and
ditolylgallium hydride.
13. A compound according to claim 12, consisting essentially of methylbenzyltelluride.
14. Methyldiphenylaluminum.
15. Methylditolylaluminum.
16. A compound according to claim 1, consisting essentially of dimethylethylgallium.
17. A compound according to claim 12, consisting essentially of dimethylethylthallium.
18. A compound according to claim 12, consisting essentially of methylphenylgallium hydride.
19. A compound according to claim 12, consisting essentially of ditolylgallium hydride.

* * * * *

UNITED STATES PATENT AND TRADEMARK OFFICE
CERTIFICATE OF CORRECTION

PATENT NO. : 4,720,560

DATED : January 19, 1988

INVENTOR(S) : Hui et al.

It is certified that error appears in the above-identified patent and that said Letters Patent is hereby corrected as shown below:

In column 4, line 36, after "following:" should be
--dimethylehylgallium
  dimethylethylindium
  diethylmethylindium--.

Signed and Sealed this

Twenty-fourth Day of October, 1989

Attest:

DONALD J. QUIGG

Attesting Officer

Commissioner of Patents and Trademarks